United States Patent [19]

Jones

[11] Patent Number: 5,016,626
[45] Date of Patent: May 21, 1991

[54] VENTILATORS FOR PROMOTING LUNG FUNCTION

[75] Inventor: Norman S. Jones, Stanbridge, England

[73] Assignee: Instruments and Movements Limited, London, England

[21] Appl. No.: 352,930

[22] Filed: May 17, 1989

[30] Foreign Application Priority Data

May 23, 1988 [GB] United Kingdom ............... 8812128

[51] Int. Cl.$^5$ ............................................. A61M 16/00
[52] U.S. Cl. ........................... 128/204.26; 128/204.23
[58] Field of Search ...................... 128/204.26, 204.23, 128/204.18

[56] References Cited

U.S. PATENT DOCUMENTS

| | | | |
|---|---|---|---|
| 3,881,480 | 5/1975 | Lafourcade . | |
| 4,003,377 | 1/1977 | Dahl | 128/204.23 |
| 4,050,458 | 9/1977 | Friend | 128/204.23 |
| 4,141,356 | 2/1979 | Smargiassi | 128/204.23 |
| 4,932,402 | 6/1990 | Snook et al. | 128/204.23 |

Primary Examiner—Edgar S. Burr
Assistant Examiner—E. P. Raciti
Attorney, Agent, or Firm—Arnold B. Silverman; David V. Radack

[57] ABSTRACT

A lung ventilator system has a demand valve to provide for spontaneous breathing with modification of the ventilator action to complement the spontaneous breathing and to synchronize restored forced ventilation with a last spontaneous breath. The system includes means to detect gas flow in the supply to the demand valve and to output a signal to the oscillator to modify or inhibit its operation in relation to the volume of gas drawn from the demand valve to vary the duration of the exhalation phase of the ventilation cycle. The system preferably uses a pneumatic oscillator with a feedback circuit connected to be influenced by the pressure drop across a restriction in the supply to the demand valve, signalled by the operation of selected ones of a plurality of inhibitor valves responding to different pressure drop levels.

10 Claims, 2 Drawing Sheets

VENTILATORS FOR PROMOTING LUNG FUNCTION

BACKGROUND OF THE INVENTION

1. Field of the Invention

THIS INVENTION concerns ventilators for inducing or assisting lung function in human patients.

2. Background Discussion and the Prior Art

For certain applications there is a requirement for a resuscitator/ventilator system that is sensitive to any spontaneous breathing efforts by the patient so as to respond to such efforts by modifying or inhibiting the operation of the system so that it does not hamper or conflict with the patient's attempt to breathe spontaneously. There are several known systems having this characteristic and two of the more well known are, the so-called Synchronised Intermittent Mandatory Ventilation (SIMV) and Mandatory Minute Ventilation (MMV) systems.

For practical utility, any such system should provide high flows with low levels of patient inspiratory effort ("demand pressure"). One arrangement for supplying breathable gas to a patient in response to a spontaneous breathing effort is to use a conventional demand valve such as used in airmen's breathing apparatus and diving equipment, this being connected in parallel with a conventional ventilator and so arranged that during the exhalation phase of the ventilator cycle, the patient can demand an inhalation volume as required.

The other required function of such a system is to modify or inhibit the ventilator action if a patient inhalation demand at the correct level occurs. However, when a demand valve is used to provide the flow for spontaneous breathing the use of a further demand detector to generate a signal to modify or inhibit the ventilator action would decrease its sensitivity.

SUMMARY OF THE INVENTION

One object of the invention is, therefore, to provide in a ventilator system having a demand valve to permit spontaneous breathing by the patient, means for modifying the ventilator action in response to gas flow satisfying a spontaneous patient demand, without prejudice to the sensitivity of the demand valve.

In one aspect, therefore, the present invention provides a ventilator system comprising a pneumatic oscillator controlling breathable gas flow in a flow path from a source to an output; a demand valve in parallel with said oscillator; and means for detecting gas flow in the supply to the demand valve and adapted to output a signal to the oscillator to modify or inhibit the operation thereof in relation to the volume of gas taken from the demand valve, to vary the duration of the exhalation phase of the ventilation cycle of the oscillator.

A further object of the present invention is to provide a ventilator system having provision for demand flow, utilising a simple and reliable pneumatic oscillator to provide the gas pulse train for forced ventilation and controlled by a simple pneumatic flow detector in a demand supply flow path so as to provide outputs appropriate to forced ventilation and at different levels of spontaneous breathing.

Thus, a ventilator system in accordance with a further aspect of the present invention comprises a pneumatic oscillator having an operating piston or equivalent controlling breathable gas flow in a flow path from a source to an output and that is responsive to feedback pressure derived from the output supplementing a bias force tending to close the flow path in opposition to the source pressure a demand valve in parallel with said oscillator; a flow restriction in the supply to the demand valve; a differential pressure sensor connected to respond to the pressure differential across said flow restriction: and a plurality of inhibitor valves arranged to be actuated by said differential pressure sensor at respectively different values of sensed pressure differential, said inhibitor valves being arranged to affect the feedback control of the oscillator selectively to vary the duration of the exhalation phase of the ventilation cycle thereof.

There may be two or more than two inhibitor valves each arranged to be operated at an individual value of the pressure differential sensed by the pressure differential sensor. Because the sensed pressure differential is a function of the depth of a spontaneous inhalation via the demand valve, the inhibitor valves can be arranged so as to affect the feedback control of the oscillator as to adjust the exhalation phase duration of the oscillator cycle to complement the breathing effort of the patient, however that effort may vary over a period of time.

Preferably the inhibitor valves affect the feedback control of the oscillator by opening a path from the gas source to the feedback circuit so as to simulate feedback derived from the output of the oscillator.

The restriction in the supply line to the demand valve and across which the pressure differential is generated to actuate the inhibitor valves may take various forms. However if it is a simple restrictor with typical non-linear flow characteristics, it is preferably bridged by a pressure relief valve that opens when the pressure differential across the restriction reaches a prescribed value, so as to allow relatively unimpeded high demand flows. Such an arrangement also enables sensitivity of operation to be reliably achieved with the use of a restriction that produces relatively high pressure differentials for small demand flows without, however, large flows being impeded when these are demanded by the patient.

Preferred embodiments of the invention incorporate an "anti-panting" arrangement to delay the response of the system to brief, low volume, demands by the patient and thereby prevent the ventilator action being inhibited in response to attempts by the patient to "pant": that is, to take repeated very short and shallow breaths that accomplish little or no effective ventilation of the lungs. This arrangement for instance, comprises a restriction, bridged by a non-return valve, in the low pressure connection to the pressure differential sensor.

BRIEF DESCRIPTION OF THE DRAWINGS

The invention will be further explained with reference to the accompanying drawings in which FIG. 1 diagrammatically illustrates the principles of a ventilator system embodying the invention.

DESCRIPTION OF PREFERRED EMBODIMENTS

Figure 1:
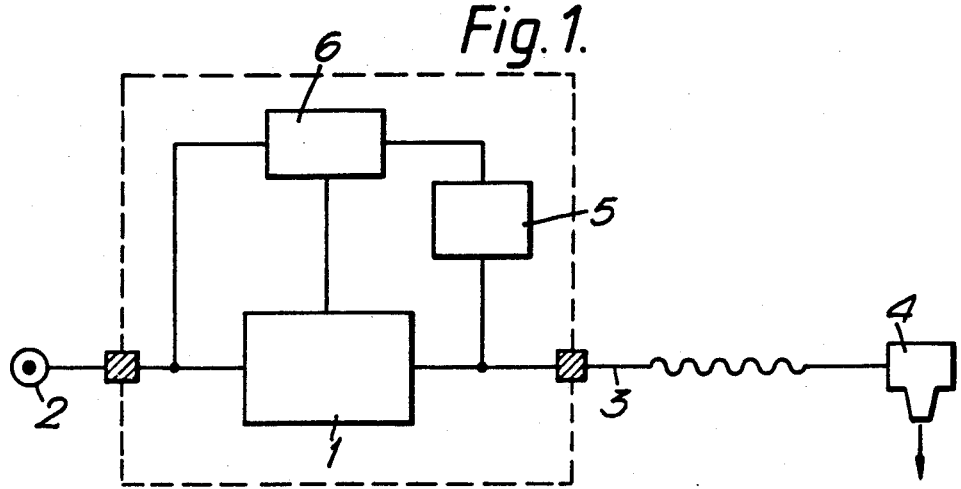

Referring to the drawings, FIG. 1 shows the principal components of a ventilator system embodying the invention. The system comprises a ventilator 1 including a pneumatic oscillator of some suitable form controlling the flow path between a pressurised gas supply 2 and an output 3 that typically extends to a patient valve 4 that in turn is connected to an oronasal mask or a tracheal intubation device. To provide for spontaneous breathing, or attempts thereat, by the patient, the flow path controlled by the ventilator 1 is bridged by a demand valve 5 the supply line to which includes a detector 6 for detecting gas flow to the demand valve and that outputs a signal to affect the operation of the ventilator 1.

The required characteristic of such a system is that when the patient makes an attempt at spontaneous breathing, the demand valve 5 opens to supply gas to satisfy that attempt, while the operation of the ventilator is inhibited or modified so as not to interfere with the attempt by the patient to breathe spontaneously.

Figure 2:
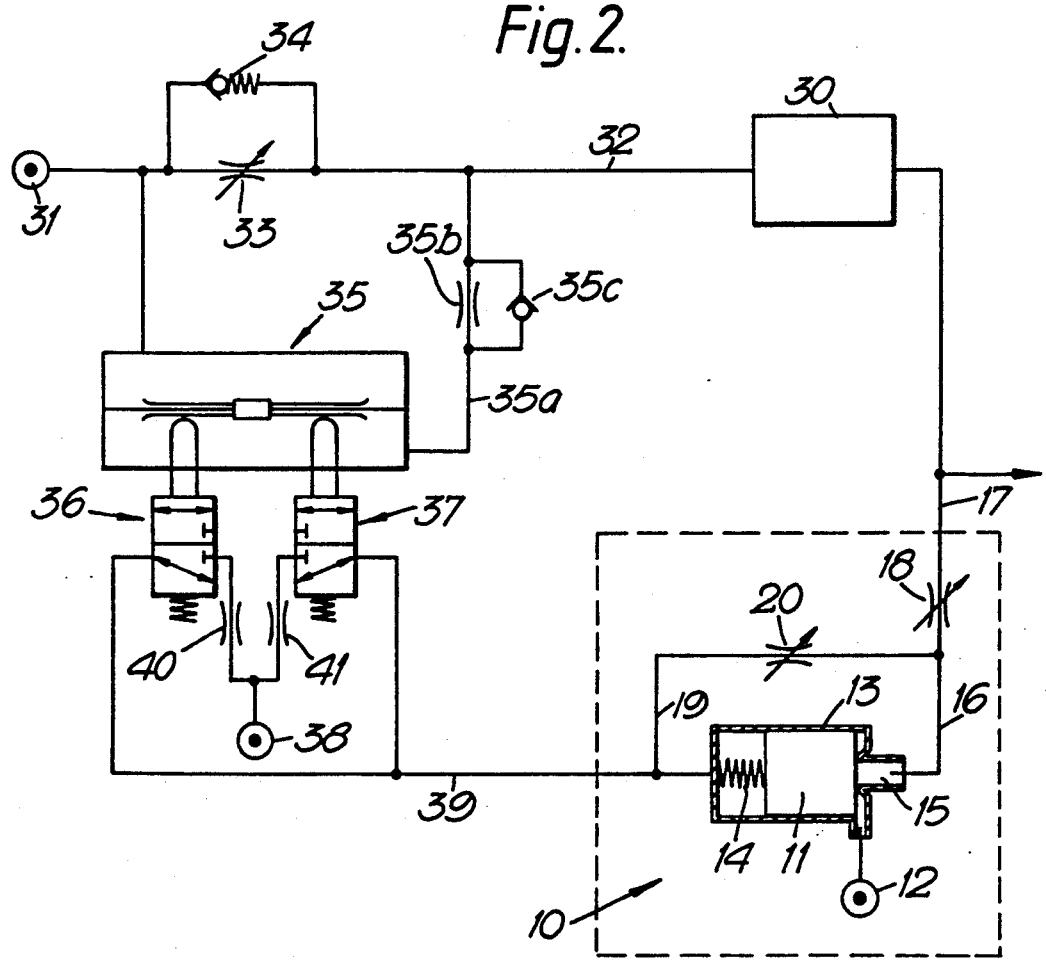
FIG. 2 illustrates a preferred embodiment of a ventilator system in accordance with the invention.

FIG. 2 illustrates a preferred embodiment of the present invention. The system shown in FIG. 2 is of the general configuration shown in FIG. 1, but is characterised in the use of a pneumatic oscillator 10 of the type, such as disclosed in FR-A-1 530 478 and U.S. Pat. No. 3,881,480, that has a biased piston or equivalent 11 movable between a flow path-closing and a flow path-opening position under the influence of the balance of forces thereon as between the pressure of the gas supply at 12, on the one hand, and the bias force as supplemented by a feedback pressure derived from the output of the oscillator. For illustration purposes the oscillator is shown as comprising a piston 11 reciprocable in a cylinder 13 and biased to a flow path closing position, to the right as seen in the drawing, by means of a spring 14. The piston 11 controls flow from the source 12 to an outlet port 15 and thence to an outlet branch 16 connected both to an output line 17 via a restrictor 18, and to a feedback line 19 via a restrictor 20.

In operation of such an oscillator to produce a train of output pressure pulses for forced ventilation, source pressure acting on the outer annular area of the right hand end of the piston overcomes the bias force provided by spring 14 to move the piston to the left as seen in the drawing to open a flow path from the source 12 to the outlet port 15, and to expose the whole right hand end of the piston to source pressure. Gas then flows through the outlet branch 16 and restrictor 18 to the patient, and also via feedback line 19 to the left hand end of cylinder 13 at a rate determined by the restrictor 20.

Gas pressure thus builds up in the left hand end of the cylinder and acts on the corresponding end of the piston 11 to supplement the bias force thereon due to the spring 14. Eventually the balance of forces on the piston causes this to move to the right to engage a sealing lip around the port 15 and thereby cut off flow to the latter and to the outlet branch 16. The drawing shows the oscillator in this condition.

An exhalation phase now commences. The pressure in the left hand end of the cylinder decays by flow through restrictors 20 and 18 and eventually the force balance on the piston reverses and it moves once again to the left to initiate a further inhalation phase.

The oscillator may be embodied in various forms in practical devices For instance, the restrictor 20 may be replaced by various restrictor/non-return valve networks to achieve particular cycling patterns in the output and to provide different operator control possibilities. The biasing of the piston may be achieved by means other than a spring: for instance the piston may have different areas effective at its opposite ends so that when both ends are exposed to the same pressure there is a net thrust towards the flow path-closing position. The piston may be replaced by an equivalent diaphragm arrangement. Whereas in the arrangement illustrated the port 15 constitutes the outlet it may instead constitute the inlet from the gas source.

Preferably the pneumatic oscillator 12 embodies the features of the inventions that are the respective subjects of copending patent applications Ser. Nos. 07/556,303 filed July 20, 1990 and 07/352,966 filed May 17. 1989. (Attorney's Dockets 105682 and 105683), herein incorporated by reference.

The system shown in FIG. 2 further comprises a demand valve 30 of any suitable type that is connected to the output line 17 and draws breathable gas from the same source as the oscillator, shown as a terminal 31, via a supply line 32 incorporating a restrictor 33 that, preferably, is bridged by a by-pass pressure relief valve 34.

In this embodiment, the demand gas flow detector is constituted by a pressure differential sensor 35 and that may for instance be a diaphragm device as illustrated or a piston device, that is connected across the restriction 33 in the supply line 32 to the demand valve, so as to respond to pressure differentials generated across the restriction 33 by flow from the terminal 31 through line 32 to the demand valve 30.

The restriction 33 may be a simple throttle or like flow restrictor and, as noted, the restriction 33 is preferably bridged by the pressure relief valve 34 that is arranged to open when the pressure differential across the restrictor 33 reaches a predetermined value, thereby to prevent unwanted impedance of high demand flows.

In the embodiment illustrated, the pressure differential sensor 35 is associated with a pair of inhibitor valves 36, 37 that are arranged to open at different levels of pressure differential as sensed by the sensor 35.

The inhibitor valves 36, 37 each control the flow of gas from a source terminal 38 to a line 39 connected to the feedback line 19 of the oscillator 10. The respective connections of the valves 36, 37 to the line 39 include individual restrictors 40, 41 that determine the rate at which gas can flow to the line 39 when its associated inhibitor valve is open.

In operation of the embodiment illustrated, any attempt by the patient to breathe spontaneously during the exhalation phase of a forced ventilation cycle of the oscillator 10 results in opening of the demand valve 30 and a flow of gas through the restriction 33. This generates a pressure differential sensed by the sensor 35 that responds by opening one or both of the valves 36 and 37 in accordance with the level of the pressure differential sensed. Opening of one or both valves 36, 37 causes gas to flow to the feedback line 19 while the pressure differential persists, to maintain or supplement the residual pressure derived from the preceding forced ventilation output gas pulse of the oscillator, on the left hand end of the cylinder 13 and thus delay, to an extent dependent on the demand flow rate and the duration of the demanded flow (i.e. to an extent dependent on the gas volume drawn through the demand valve), the instant at which the balance of forces on the piston allows this to be moved to the left by the source pressure acting on its right hand end, to initiate another forced ventilation output gas pulse.

A pressure differential that signifies a relatively weak spontaneous breathing effort by the patient will, for instance, cause only the valve 36 to open. The restrictor 40 associated with the valve 36 is sized such that the flow to the feedback line 19 is sufficient to delay movement of the piston 11 to the left, as seen in the drawing, to initiate a new inhalation phase of forced ventilation, only to an appropriate extent to allow for exhalation by the patient: that is the exhalation phase of the forced ventilation cycle in which the spontaneous inhalation through the demand valve occurs is slightly extended to accommodate exhalation of the spontaneous breath taken during that exhalation phase.

However, a stronger spontaneous breathing effort (greater demand flow) creates a larger pressure differential and opens also the valve 37 so that a greater flow to the feedback line 19 occurs and the movement of the piston 11 to terminate the forced ventilation exhalation phase in which the spontaneous inhalation occurred is more delayed for a given duration of the spontaneous inhalation causing the demand flow.

Thus, if during the exhalation phase of forced ventilation the patient makes a spontaneous effort to inhale and draws a gas volume through the demand valve in excess of a threshold level, this gas flow through the demand valve modifies or inhibits the oscillator action. For low levels of spontaneous breathing effort above the threshold, the oscillator action is modified by appropriate extension of the exhalation phase to allow for exhaling of the spontaneous breath, whereupon the oscillator initiates a further forced inhalation phase to complement the spontaneous effort. However, should the patient commence strong spontaneous breathing, such that a second spontaneous breath is commenced before the termination of the (extended) exhalation phase of the oscillator action, this exhalation phase will be further extended. The oscillator action will thus effectively be inhibited for so long as the strong spontaneous breathing continues. However, should this spontaneous breathing falter, the inhibition of the oscillator will cease and forced ventilation will resume, the first forced ventilation inhalation phase being initiated after a period of time, following the last spontaneous breath, that is determined by the depth of that last breath.

There may be more than the two inhibitor valves 36, 37 illustrated so as to provide varying degrees in delay of a succeeding forced ventilation inhalation phase, to complement various depths of spontaneous breathing as sensed by the pressure differential generated across the restriction 33. However, in most cases, two valves will suffice, one (e.g. valve 36) arranged to open at a first pressure differential threshold corresponding approximately with a demand flow rate equal to one half the flow rate provided in a forced ventilation inhalation phase, this valve being associated with a restrictor (40) so sized in relation to the restrictors 18 and 20 as to cause the initiation of a further forced inhalation phase after a period, following cessation of the demand flow, having a maximum duration that corresponds to the exhalation phase duration in forced ventilation in the absence of a spontaneous breathing attempt, and attained in the case of a demand flow that persists for the duration of a forced inhalation. With such an arrangement for the first inhibitor valve, the second inhibitor valve (e.g. valve 37) may be arranged to open at a second, higher, pressure differential threshold corresponding approximately with a demand flow rate equal to the flow rate provided in a forced inhalation, and be associated with a restrictor (41) so sized in relation to the restrictors 18, 20 and 40 as to cause initiation of the next forced inhalation phase after a period following closure of the two inhibitor valves that has a maximum duration equal to the forced ventilation exhalation phase duration if the second valve remains open for one half the duration of a forced inhalation.

With the two inhibitor valves so aranged and calibrated, it will be understood that the ventilator action will be modified if the patient makes a spontaneous effort to inhale with a demand flow rate equal to or exceeding one half that provided in forced ventilation. If in a spontaneous inhalation the patient draws a tidal volume equal to or exceeding about one half that provided in a forced inhalation, whether by a short deep breath or by an extended shallow breath, the ventilator action will be modified to provide an exhalation period, following the spontaneous inhalation, equal to that provided during forced ventilation.

The inhibitor valves will usually be spring-return poppet valves but any suitable valve type may be used for this purpose.

Patients undergoing forced ventilation occasionally respond by attempting to "pant": that is, to take repeated short duration shallow breaths that produce negligible lung ventilation, the tidal flow of fresh gas being confined to oronasal passages and the windpipe. It is, therefore, undesirable for a ventilator to cease its regular forced ventilation pattern as a consequence of the onset of panting.

In preferred embodiments of the system of this invention, the response of the inhibitor valves to spontaneous breathing effort is delayed so as to prevent an effective response to a very short, low volume, inhalation effort by the patient.

Thus, as shown in FIG. 2, the low pressure connection to the sensor 35, that is, the line 35a extending from the line 32 between the demand valve 30 and the restriction 33, incorporates a restriction 35b that is bridged by a non-return valve 35c. This arrangement delays the reduction of pressure in the sensor 35 by restricting flow therefrom, and this delays the response of the inhibitor valves 36, 37 to a pressure differential appearing across the restriction 33. The non-return valve 35c, however, enables rapid restoration of pressure in the sensor when demand flow ceases, as between "panting" breaths, so that a succession of "panting" breaths cannot cumulatively operate the inhibitor valves.

In practice a ventilator system as illustrated has been found to work well in simulated trials. If the operating parameters are set for satisfactory operation with an adult patient, it will usually be necessary to provide for a lower inhalation phase gas flow rate if the ventilator is to be used for a child patient. In general, the inhalation phase gas flow rate can be adjusted by adjustment of the restrictor 18 in the output of the oscillator 10. However although the ventilation flow may be reduced by this expedient, the breathing effort required to modify or inhibit the ventilator action, being determined by restriction 33, may then be too high.

Accordingly the restriction 33 may be made adjustable so as to make it possible to adjust the breathing effort level for modification/inhibition of ventilator action. Preferably the restrictor 18 and restriction 33 would be arranged for adjustment in synchronism, as by being ganged, so that an adjustment of the restrictor 18 would be complemented by an appropriate adjustment of the restriction 33.

Figure 3:
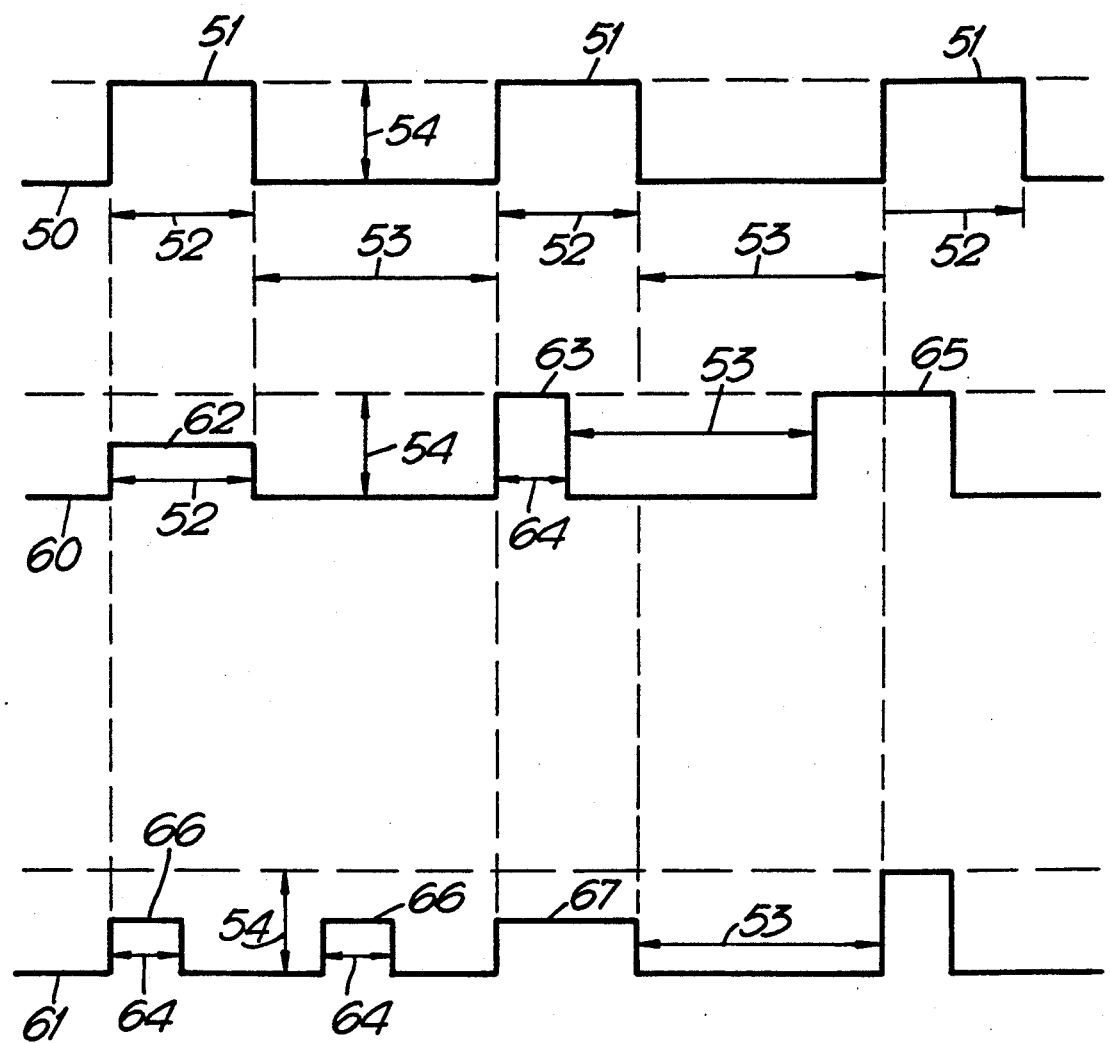
FIG. 3 is a timing and gas flow diagram.

Typical flow traces for simulations of the ventilation mode and for the demand/inhibiting mode with a ventilator system conforming with FIG. 2 and with the inhibitor valves 36, 37 and their respective associated restrictors 40, 41 calibrated as above described, are shown in FIG. 3. In practice the demand breaths will not be square waves as shown, so that the demand volume will be rather greater than shown to achieve a given reduction of exhalation time. These traces show, in line 50, the regular forced ventilation gas pulses 51 produced by the fundamental oscillator action, each pulse occupying a set inhalation period 52 followed by a set exhalation period 53. Each pulse 51 has a standard flow rate represented by the height 54.

The trace lines 60, 61 show the consequences of various spontaneous breathing efforts by a patient. Thus line 60 shows a demand breath 62 at a flow rate one half that of a forced inhalation (54), but for a duration 52 corresponding with that of a forced inhalation. As a consequence of the opening of valve 36 for the duration of the breath 62, this breath 62 is then followed by an exhalation period corresponding in length with the forced ventilation exhalation period 53.

Next there is shown a breath 63 having the standard flow rate 54 but a duration 64 one half that of the set period 52 for forced inhalation. As a consequence of both valves 36 and 37 being open for the duration of the breath 63, this breath 63 is also followed by the exhalation period 53. The breath 65 on line 60 corresponds in flow rate 54 and duration 52 with the regular forced inhalation 51.

On line 61 a pair of breaths 66 of flow rate one half 54 and duration one half 52 are shown to be followed by exhalation periods that are one half the forced ventilation exhalation period 53, while a subsequent breath 67 of half normal flow rate 54 but full duration 52 (i.e. as breath 62) is shown to be followed by the normal exhalation period 53.

I claim:

1. A ventilator system comprising a pneumatic oscillator controlling breathable gas flow in a flow path from a source to an output, said oscillator providing a ventilation cycle consisting of an exhalation phase having a first duration and an inhalation phase having a second duration; a demand valve in parallel with said oscillator, said demand valve enabling demand gas flow therethrough in response to a demand for gas at said output; and means for detecting gas flow in the supply to the demand valve and adapted to output a signal to the oscillator to modify or inhibit the operation thereof in relation to the volume of demand has taken from the demand valve, to vary said first duration of said exhalation phase of said ventilation cycle of the oscillator.

2. A ventilator system comprising a pneumatic oscillator having an operating piston or equivalent controlling breathable gas flow in a flow path from a source to an output and that is responsive to feedback pressure derived from the output supplementing a bias force tending to close the flow path in opposition to the source pressure, said oscillator providing a ventilation cycle consisting of an exhalation phase having a first duration and an inhalation phase having a second duration; a demand valve in parallel with said oscillator, said demand valve enabling demand gas flow therethrough in response to a demand for gas at said outlet; a flow restriction between said source and the demand valve; a differential pressure sensor having a low pressure connection between said flow restriction and said demand valve and connected to respond to a pressure differential across said flow restriction; and a plurality of inhibitor valves arranged to be actuated by said differential pressure sensor at respectively different values of sensed pressure differential, said inhibitor valves being arranged to affect said feedback pressure selectively to vary said first duration of said exhalation phase of said ventilation cycle thereof.

3. The ventilator system of claim 2, including a plurality of individual gas pathways from said gas source to said operating piston or equivalent, an individual said inhibitor valve being disposed in each said pathway, whereby opening of a said inhibitor valve allows gas to flow from said source to said operating piston or equivalent to supplement feedback pressure derived from the output of the oscillator.

4. The ventilator system of claim 2, including a pressure relief valve bridging said flow restriction, said pressure relief valve being arranged to open when the pressure differential across said flow restriction reaches a predetermined value, thereby to resist undesired impedance of high demand gas flows.

5. The ventilator system of claim 3, including a pressure relief valve bridging said flow restriction, said pressure relief valve being arranged to open when the pressure differential across said flow restriction reaches a predetermined value, thereby to resist undesired impedance of high demand gas flows.

6. The ventilator system of claim 2, including means for adjusting the inhalation phase gas flow rate output by the oscillator.

7. The ventilator system of claim 2, including means for varying the demand gas flow rate at which operation of the inhibitor valves occurs.

8. The ventilator system of claim 2, including means for adjusting the inhalation phase gas flow rate output by the oscillator and means for varying the demand gas flow rate at which operation of the inhibitor valves occurs, said inhalation phase gas flow rate adjusting means being arranged to operate in synchronism with said demand gas flow rate varying means.

9. The ventilator system of claim 1, including delay means to delay output of said signal in response to a detected demand gas flow.

10. The ventilator system of claim 2, including delay means comprising (i) a delay means flow restriction in said low pressure connection and (ii) a non-return valve bridging said delay means flow restriction, said non-return valve permitting rapid restoration of pressure at said differential pressure sensor.

* * * * *

UNITED STATES PATENT OFFICE
CERTIFICATE OF CORRECTION

PATENT NO. : 5,016,626

DATED : May 21, 1991

INVENTOR(S) : NORMAN S. JONES

It is certified that error appears in the above-identified patent and that said Letters Patent is hereby corrected as shown below:

Column 2, line 3, a semicolon --;-- should be inserted after "pressure".

Column 2, line 7, the colon ":" should be a semicolon --;--.

Column 3, line 61, a period --.-- should be inserted after "devices".

Column 4, line 10, "17." should be --17,--.

Claim 1, column 7, line 47, "has" should be --gas--.

Signed and Sealed this

Twenty-second Day of December, 1992

Attest:

DOUGLAS B. COMER

*Attesting Officer*   *Acting Commissioner of Patents and Trademarks*